United States Patent [19]

Whittaker

[11] 4,448,967

[45] May 15, 1984

[54] PROCESS FOR PREPARING CHLORO-TRIFLUOROMETHYL PYRIDINES

[75] Inventor: Graham Whittaker, Cheshire, England

[73] Assignee: Imperial Chemical Industries PLC, London, England

[21] Appl. No.: 409,854

[22] Filed: Aug. 20, 1982

[30] Foreign Application Priority Data

Sep. 3, 1981 [GB] United Kingdom ............... 8126746

[51] Int. Cl.³ ........................................... C07D 213/26
[52] U.S. Cl. .................................... 546/345; 546/346
[58] Field of Search ............................. 546/345, 346

[56] References Cited

U.S. PATENT DOCUMENTS

| | | | |
|---|---|---|---|
| 4,266,064 | 5/1981 | Nishiyama et al. | 546/345 |
| 4,288,600 | 9/1981 | Roberts et al. | 546/345 |
| 4,393,214 | 7/1983 | Roberts et al. | 546/345 |

*Primary Examiner*—Alan L. Rotman
*Attorney, Agent, or Firm*—Cushman, Darby & Cushman

[57] ABSTRACT

3-Chloro-5-trifluoromethylpyridine and/or 2,3-dichloro-5-trifluoromethylpyridine are produced by selective vapor-phase chlorination of 3-trifluoromethylpyridine or 2-chloro-5-trifluoromethylpyridine in the presence of a copper catalyst.

4 Claims, No Drawings

PROCESS FOR PREPARING CHLORO-TRIFLUOROMETHYL PYRIDINES

This invention relates to the production of chlorotrifluoromethylpyridines.

The compound 2,3-dichloro-5-trifluoromethylpyridine is a useful intermediate in the preparation of compounds having herbicidal activity, for example compounds described in European Patent Publication No. 0001473. The compound 3-chloro-5-trifluoromethylpyridine is in turn useful in the preparation of the said intermediate via further ring-chlorination.

It is known that 3-trifluoromethylpyridine may be selectively chlorinated to yield 2-chloro-5-trifluoromethylpyridine (as described in European Patent Publication No. 0013474 but 3-chloro-5-trifluoromethylpyridine is not reported among the products of this process.

We have now found that when the chlorination of 3-trifluoromethylpyridine or 2-chloro-5-trifluoromethylpyridine is carried out in the presence of a copper catalyst there is a degree of selectivity towards chlorination in the $\beta$-position other than that occupied by the trifluoromethyl group. Thus 3-trifluoromethylpyridine may be chlorinated to yield 3-chloro-5-trifluoromethylpyridine and/or 2,3-dichloro-5-trifluoromethylpyridine; similarly 2-chloro-5-trifluoromethylpyridine may be chlorinated to yield 2,3-dichloro-5-trifluoromethylpyridine.

Thus according to the present invention there is provided a process for the production of 3-chloro-5-trifluoromethylpyridine and/or 2,3-dichloro-5-trifluoromethylpyridine characterised in that 3-trifluoromethylpyridine or 2-chloro-5-trifluoromethylpyridine is reacted with chlorine in the vapour phase at a temperature in the range from 250° C. to 450° C. in the presence of a catalyst comprising an oxide, chloride or fluoride of copper.

The reaction is preferably carried out at a temperature in the range from 300° C. to 380° C.

The proportion of chlorine is preferably at least 1 mole (for example from 2 to 15 moles) of chlorine per mole of the organic starting material.

The catalyst may be used either in the form of a fixed bed or in the form of a fluidised bed. The metal oxide or halide may be unsupported or may be carried upon a support material, for example aluminium fluoride, alumina, silica or a silica-alumina.

The chlorination process is preferably carried out in the presence of an inert diluent, conveniently nitrogen (using, for example, from 2 to 20 moles of nitrogen per mole of the organic starting material) but other inorganic diluents may be used and organic diluents (for example chlorinated hydrocarbons, especially carbon tetrachloride) may also be used.

The reaction mixture may also contain a small proportion of hydrogen fluoride. This may arise, for example, when 2-chloro-5-trifluoromethylpyridine is used as starting material and this is introduced in the form of the gaseous reaction product obtained by the reaction between 3-picoline, chlorine and hydrogen fluoride (as described, for example, in U.K. patent application No. 2 045 761).

The optimum residence time will depend upon the particular catalyst employed, the reaction temperature and the relative proportions of chlorine and organic starting material; in general suitable residence times are in the range from 1 to 60 seconds.

The 3-chloro-5-trifluoromethylpyridine and/or 2-3-dichloro-5-trifluoromethylpyridine produced may, if desired, be separated from the other reaction products by conventional methods, for example fractional distillation and/or acid extraction. Chlorinated by-products may, if desired, be dechlorinated to yield 3-trifluoromethylpyridine for recycling to the chlorination process.

The invention is illustrated by the following Examples. Unless otherwise stated, all parts and percentages are by weight.

EXAMPLE 1

A catalyst was prepared by impregnation of aluminium trifluoride support (mean particle size 150 $\mu$m) with aqueous cupric chloride solution to give a catalyst containing 7.5% Cu by weight.

The catalyst (900 g) was charged to a vertical Inconel reactor (50 mm diameter, 1 m long) and fluidised with a stream of nitrogen at 300° C. for 1 hour, followed by treatment with HF (4 mol $h^{-1}$) at 300° C. for 30 min.

A stream of 3-trifluoromethylpyridine (1 mole $h^{-1}$) in nitrogen was pre-heated to 220° C. and reacted in the fluidised bed with a stream of chlorine which had similarly been pre-heated to 220° C. The reaction mixture contained 2.5 moles of chlorine and 6 moles of nitrogen per mole of 3-trifluoromethylpyridine. The temperature of the fluidised bed was maintained at 320° C.; the residence time in the reactor was 17 sec.

Analysis of the reaction products by capillary gas chromatography showed the main products to be:

| | |
|---|---|
| unreacted 3-trifluoromethylpyridine | 31% |
| 3-chloro-5-trifluoromethyl-pyridine | 24% |
| 2,3-dichloro-5-trifluoro-methylpyridine | 4% |
| 2-chloro-5-trifluoromethyl-pyridine | 26% |

EXAMPLE 2

The catalyst was the same as described in Example 1.

A stream of 3-trifluoromethylpyridine (0.5 mole $h^{-1}$) in nitrogen was pre-heated to 220° C. and reacted in the fluidised bed with a stream of chlorine which has similarly been pre-heated to 220° C. The reaction mixture contained 9.5 moles of chlorine and 6 moles of nitrogen per mole of 3-trifluoromethylpyridine. The temperature of the fluidised bed was maintained at 360° C.; the residence time in the bed was 18 sec.

Analysis of the reaction products by capillary gas chromatography showed the main products to be:

| | |
|---|---|
| 3-chloro-5-trifluoromethyl-pyridine | 16% |
| 2,3-dichloro-5-trifluoro-methylpyridine | 21% |
| 2-chloro-5-trifluoro-methylpyridine | 24% |
| 2,5-dichloro-3-trifluoro-methylpyridine | 10% |

EXAMPLE 3

A stream of 2-chloro-5-trifluoromethylpyridine (0.6 mole $h^{-1}$) in nitrogen was pre-heated to 220° C. and reacted in the fluidised bed with a stream of chlorine which had similarly been pre-heated to 220° C. The reaction mixture contained 7.5 moles of chlorine and 6 moles of nitrogen per mole of 2-chloro-5-trifluoromethylpyridine. The temperature of the fluidised bed of catalyst (as described in Example 1) was maintained at 360° C.; the residence time was 17 sec.

Analysis of the reaction products by capillary gas chromatography showed the main products to be:

| | |
|---|---|
| unreacted 2-chloro-5-trifluoromethyl-pyridine | 50% |
| 2,3-dichloro-5-trifluoro-methylpyridine | 15% |
| 2,6-dichloro-3-trifluoro-methylpyridine | 8% |
| 2-fluoro-5-trifluoromethyl-pyridine | 11% |

I claim:

1. A process for the production of at least one of the compounds 3-chloro-5-trifluoromethylpyridine and 2,3-dichloro-5-trifluoromethylpyridine which comprises reacting a substituted pyridine selected from the group consisting of 3-trifluoromethylpyridine and 2-chloro-5-trifluoromethylpyridine with at least one mole of chlorine per mole of substituted pyridine in the vapour phase at a temperature in the range from 250° C. to 450° C. in the presence of a catalyst comprising an oxide, chloride or fluoride of copper.

2. A process according to claim 1 wherein the reaction temperature is in the range from 300° C. to 380° C.

3. A process according to claim 1 wherein the proportion of chlorine is from 2 to 15 moles per mole of the said starting material.

4. A process according to claim 1 wherein the reaction is carried out in the presence of an inert gaseous diluent.

* * * * *